(12) United States Patent
Boisvilliers

(10) Patent No.: US 12,397,308 B2
(45) Date of Patent: Aug. 26, 2025

(54) METHOD FOR ANALYSING A SPRAY GENERATED BY A DEVICE FOR DISPENSING FLUID PHARMACEUTICAL PRODUCT

(71) Applicant: APTAR FRANCE SAS, Le Neubourg (FR)

(72) Inventor: Julien Boisvilliers, Crosville la Vieille (FR)

(73) Assignee: APTAR FRANCE SAS, Le Neubourg (FR)

( * ) Notice: Subject to any disclaimer, the term of this patent is extended or adjusted under 35 U.S.C. 154(b) by 347 days.

(21) Appl. No.: 17/960,345

(22) Filed: Oct. 5, 2022

(65) Prior Publication Data

US 2023/0123194 A1    Apr. 20, 2023

Related U.S. Application Data

(63) Continuation-in-part of application No. 16/477,300, filed as application No. PCT/FR2018/050074 on Jan. 12, 2018, now abandoned.

(30) Foreign Application Priority Data

Jan. 16, 2017    (FR) ...................... 1750318

(51) Int. Cl.
*B05B 12/08*    (2006.01)
*A61M 11/00*    (2006.01)
(Continued)

(52) U.S. Cl.
CPC .......... *B05B 12/082* (2013.01); *A61M 11/00* (2013.01); *G06T 7/001* (2013.01); *G06T 7/60* (2013.01);
(Continued)

(58) Field of Classification Search
CPC ....... C12Q 1/04; B05B 12/084; B05B 12/082; G01N 21/455; G01N 33/483; A61M 15/08; A61M 2209/02; G01M 99/008
See application file for complete search history.

(56) References Cited

U.S. PATENT DOCUMENTS

| | | | |
|---|---|---|---|
| 6,973,199 B2 | 12/2005 | Farina | |
| 2004/0131243 A1* | 7/2004 | Farina | ..................... G01P 5/001 382/141 |
| 2013/0257966 A1* | 10/2013 | Rzadca | .................. B41J 2/2142 347/19 |

OTHER PUBLICATIONS

English Translation of International Preliminary Report on Patentability issued from the International Bureau in counterpart International Application No. PCT/FR2018/050074, dated Apr. 3, 2019.
(Continued)

*Primary Examiner* — Hwa Andrew Lee
(74) *Attorney, Agent, or Firm* — Sughrue Mion, PLLC

(57) ABSTRACT

A method of analyzing a spray generated by a spray device for spraying pharmaceutical fluid, including providing a spray head of a spray device for spraying pharmaceutical fluid, the spray head including a spray orifice; causing a test fluid to pass through the spray head towards the spray orifice, the test fluid being air at a temperature that is different from ambient temperature; displaying, by strioscopy, the flow of test fluid leaving the spray orifice; and analyzing the display of the test-fluid flow so as to determine whether or not the test-fluid spray coming from the spray head complies with predetermined specifications. The cycle time for analyzing one spray head is less than 1.5 seconds, advantageously less than 1 second.

22 Claims, 3 Drawing Sheets

(51) Int. Cl.
*G06T 7/00* (2017.01)
*G06T 7/60* (2017.01)
*G06T 9/00* (2006.01)

(52) U.S. Cl.
CPC ....... *G06T 9/00* (2013.01); *A61M 2205/3334* (2013.01); *A61M 2205/70* (2013.01); *G06T 2207/30164* (2013.01)

(56) References Cited

OTHER PUBLICATIONS

International Search Report for PCT/FR2018/050074 dated May 25, 2018 PCT/ISA/210.
Vincent Faivre et al., "Experimental and numerical Investigations of jet active control for combustion applications", Journal of Turbulence, Institute of Physics Publishing, XP001538482, Aug. 5, 2004, vol. 5, No. 25.

* cited by examiner

METHOD FOR ANALYSING A SPRAY GENERATED BY A DEVICE FOR DISPENSING FLUID PHARMACEUTICAL PRODUCT

CROSS-REFERENCE TO RELATED APPLICATIONS

This application is a continuation-in-part of U.S. application Ser. No. 16/477,300, filed Jul. 11, 2019, which is a national stage of PCT/FR2018/050074, filed Jan. 12, 2018 and claims priority under 35 U.S.C. § 119 to French Patent Application No. FR 1750318, filed on Jan. 16, 2016, the disclosures of which are incorporated by reference herein in their entireties.

FIELD OF INVENTION

The present invention relates to a dispenser, and to a method of analyzing a spray generated by a spray device for spraying a pharmaceutical fluid.

BACKGROUND

Spray devices for spraying pharmaceutical fluid are well known. In particular in nasal-spray applications, the therapeutic effectiveness of the sprayed fluid may depend on the properties of the spray generated while the device is being actuated. In known manner, at the end of the assembly line, i.e. once the spray device is assembled, and just prior to being sent to the pharmaceutical-fluid manufacturer for assembly onto a corresponding reservoir, a certain number of samples of assembled devices are laboratory tested so as to verify whether the properties of the spray correspond to pre-defined specifications.

A drawback of that system is that is relates to assembled devices, and thus destroys the devices which, after being tested, can no longer be delivered to the customer. Furthermore, the system requires human verification of the tested devices, and is thus not suitable for being completely automated.

The document "Assessment of fuel spraying using schlieren system" by Marek Klimkiewicz, Agriculture No. 65, Vol. 2015, pp. 119-126, describes the use of strioscopy to analyze fuel sprays coming from various fuel injectors.

CERTAIN OBJECTS OF INVENTION

An object of the present invention is to overcome the above-mentioned drawbacks.

In particular, an object of the present invention is to provide a device and a method of analyzing spray that do not destroy the tested devices.

Another object of the present invention is to provide a device and a method of analyzing spray that is largely automated.

Another object of the present invention is to provide a device and a method of analyzing spray that has a very short cycle time, thus allowing analysis of 100% of the devices on an assembly line.

Another object of the present invention is to provide a device and a method of analyzing spray that is simple and/or inexpensive to manufacture, to assemble, and to use.

The present invention thus provides a method of analyzing a spray generated by a spray device for spraying pharmaceutical fluid, the method comprising the following steps:

providing a spray head of a spray device for spraying pharmaceutical fluid, said spray head including a spray orifice;

causing a test fluid to pass through said spray head towards said spray orifice, said test fluid being air at a temperature that is different from ambient temperature;

displaying, by strioscopy, the flow of test fluid leaving said spray orifice; and analyzing said display of the test-fluid flow so as to determine whether or not the test-fluid spray coming from said spray head complies with predetermined specifications, wherein the cycle time for analyzing one spray head is less than 1.5 seconds, advantageously less than 1 second.

Advantageously, said analyzing step includes determining the cone angle of the test-fluid spray.

Advantageously, said analyzing step includes an image-processing step for processing said display of the test-fluid flow.

Advantageously, said predetermined specifications include a predetermined spray cone angle, such that test-fluid sprays having a cone angle that is greater than or equal to said predetermined spray cone angle are classed as being compliant, and test-fluid sprays having a cone angle that is less than said predetermined spray cone angle are classed as being non-compliant.

Advantageously, a complete cycle comprises following steps:

the plate supporting a spray head is moved to place a spray head in the analyzing device;

once the plate supporting the spray head has stopped, a request for the acquisition of a reference images is made;

one reference image is taken before the air flow generator is actuated;

after that first reference image without air flow has been taken, the air flow generator is actuated;

once the air flow generator generates a stationary air flow, two reference images are taken;

these two reference images are then superimposed with the first reference image taken without air flow, and an image processing step is started;

after the image processing, the images are compressed;

the compressed images are then displayed.

Advantageously, during said movement step, one reference image is taken without any spray head, which allows to evaluate if some parts of the analyzing device must be cleaned.

Advantageously, the time for said movement step is less than 500 milliseconds, advantageously about 375 milliseconds.

Advantageously, the time for said request step is less than 300 milliseconds, advantageously less than 250 milliseconds.

Advantageously, the time to take a reference image is less than 10 milliseconds, advantageously about 7 milliseconds.

Advantageously, the time between the acquisition of a first reference image without air flow and the actuation of the air flow generator is less than 50 milliseconds, advantageously about 40 milliseconds.

Advantageously, the time between the actuation of the air flow generator and the generation of a stationary air jet is about 100 milliseconds.

Advantageously, the duration of said stationary air flow is less than 200 milliseconds, advantageously about 170 milliseconds.

Advantageously, the time for said image processing step is less than 250 milliseconds, advantageously about 220 milliseconds.

Advantageously, the time for the display step is less than 100 milliseconds, advantageously about 60 milliseconds.

Advantageously, said compressed images are saved.

Advantageously, said saving step takes about 200 milliseconds.

Advantageously, the total test phase, between the acquisition of the first reference image without air flow and the display of the compressed image, has a maximum duration which is less than 700 milliseconds with image saving and less than 500 milliseconds without image saving.

The present invention also provides a device for analyzing a spray generated by a spray device for spraying pharmaceutical fluid, the device comprising:

a spray head of a spray device for spraying pharmaceutical fluid, said spray head including a spray orifice;

generator means for generating a flow of a test fluid and passing said flow of test fluid through said spray head towards said spray orifice, said test fluid being air at a temperature that is different from ambient temperature;

a strioscopic setup for displaying, by strioscopy, the flow of test fluid leaving said spray orifice; and analyzer means for analyzing said display of the test-fluid flow so as to determine whether or not the test-fluid spray coming from said spray head complies with predetermined specifications, wherein the cycle time for analyzing one spray head is less than 1.5 seconds, advantageously less than 1 second.

Advantageously, said analyzer means include measuring means for measuring the cone angle of the test-fluid spray.

Advantageously, said analyzer means include image-processing means for processing said display of the test-fluid flow.

Advantageously, said strioscopic setup comprises a camera, an objective lens, a light source, said generator means for generating a test-fluid flow, a display zone, at least one collimator lens, and a filter.

Advantageously, said strioscopic setup further comprises a concave and/or parabolic mirror.

Advantageously, said filter is a point, a wire, or a blade.

BRIEF DESCRIPTION OF THE DRAWINGS

These characteristics and advantages and others appear more clearly from the following detailed description, given by way of non-limiting example, and with reference to the accompanying drawings, in which.

DETAILED DESCRIPTION

An object of the invention is to improve the quality of spray device inspection. To do this, the invention envisages using strioscopy to analyze in automatic manner the cone of the spray emitted by spray devices.

Strioscopy, or the schlieren method, is an optical display method that makes it possible to isolate in an image the details and small variations, in particular small variations in refractive index as happens during compression of air or other fluids. Graphically, the fundamental idea of the method is to remove light that has not been deflected by the object, e.g. the fluid under study. Specifically, only rays that have been deflected by said object correspond to turbulence or to optical high spatial frequencies. To achieve that, an image is made initially of the light source, preferably an incoherent light source, e.g. by means of a converging lens. Rays that have not been subjected to deflection (zero spatial frequencies) pass through the precise location of the geometrical image. These rays are eliminated with a filter. The other rays, those that have been deflected, are not focused at the same location and they can thus pass through in order to form a filtered image. In summary, the smooth background of the image is eliminated and consequently, the details or turbulence of the object, that were buried in the smooth background, become visible.

The filter used may merely be a point, a wire, or a blade, e.g. of the "Foucault knife-edge" type.

Strioscopy is an application of optical spatial Fourier filtering. Specifically, Fraunhofer diffraction indicates that a lens creates, in its image focal plane, the Fourier transform of the object in question. In this plane, it is thus possible to see the spatial frequencies associated with the object, and the filter is placed in the same plane in order to eliminate some of the spatial frequencies. This wave interpretation of strioscopy makes it comparable to high-pass filtering.

In the context of the present invention, the object is to show a flow of a test fluid, namely a jet of air at a temperature that is different from ambient temperature, e.g. heated air coming from the spray orifice 2 of a spray head 1 of a spray device for spraying pharmaceutical fluid, and to observe it by means of a camera. In a variant, it is also possible to use a jet of air at a temperature that is lower than ambient temperature.

Figure 1:
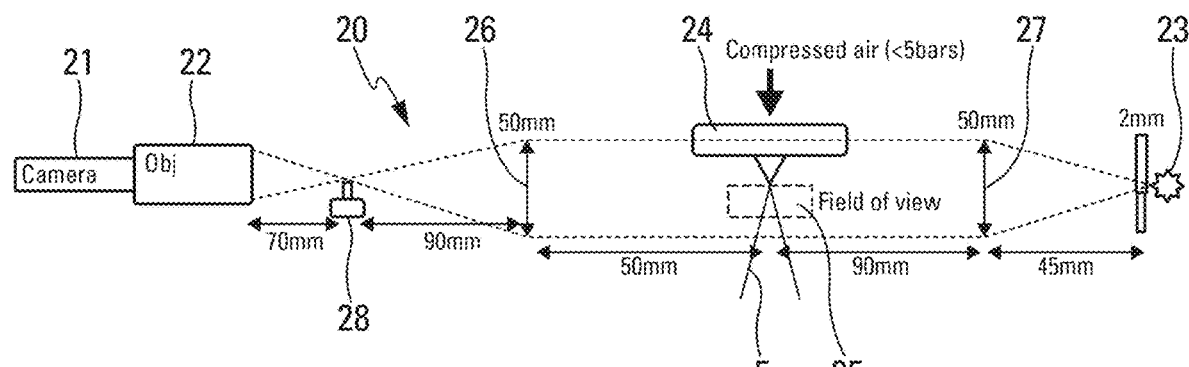
FIG. 1 is a diagrammatic view of a device for analyzing a spray, in a first advantageous embodiment.

FIG. 1 shows a strioscopic setup 20 in a first advantageous embodiment.

In this embodiment, a camera 21 associated with an objective lens 22 is arranged on one side of the setup 20, and a light source 23 is arranged on the opposite side. Generator means 24 for generating compressed air are provided so as to deliver a flow of air, preferably at a temperature that is different from ambient temperature, and pass it through a spray head 2 that is arranged in a display zone 25 that is arranged between two collimator lenses 26, 27. A blade or diaphragm 28 is provided in front of the objective lens 22 so as to interrupt the beam and thus filter the image, and thereby display the spray, as explained above.

The following components of standard type may be used for this setup:

| Components | Description |
| --- | --- |
| Camera | Manta 1292 × 964 @ 30 hertz (Hz) |
| Objective lens | 85 millimeters (mm) f: 1.8 |
| Collimator lens | 50 mm |
| Collimator lens | 50 mm |
| Lamp | White LED |
| Diaphragm | 2 mm |
| Pulse | Smartek 10 microseconds (µs), 12 amps (A) |

Figure 2:
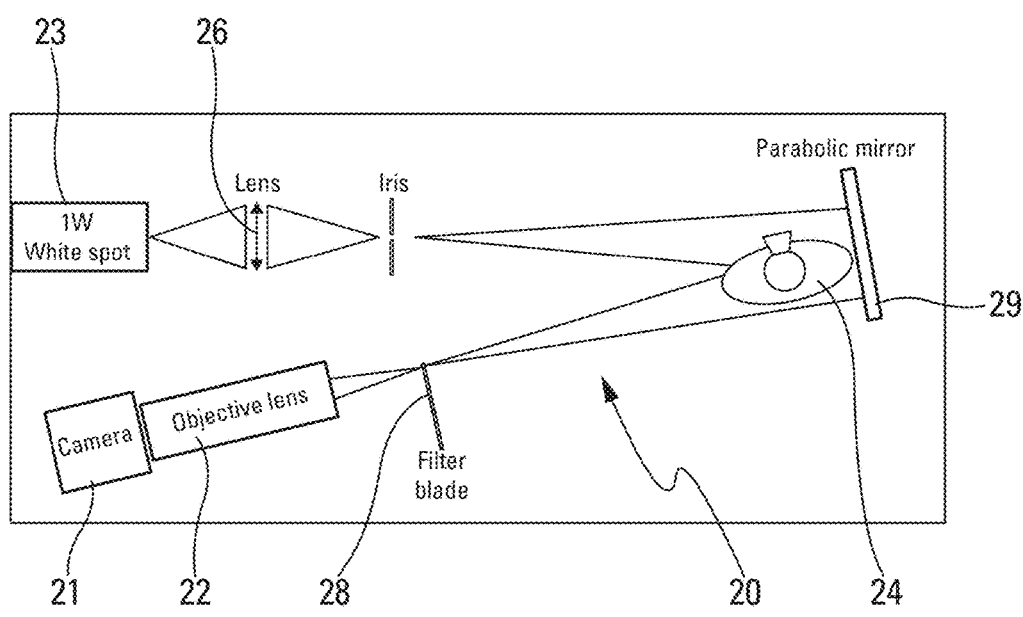
FIG. 2 is a diagrammatic view of a device for analyzing a spray, in a second advantageous embodiment.
Figure 3:
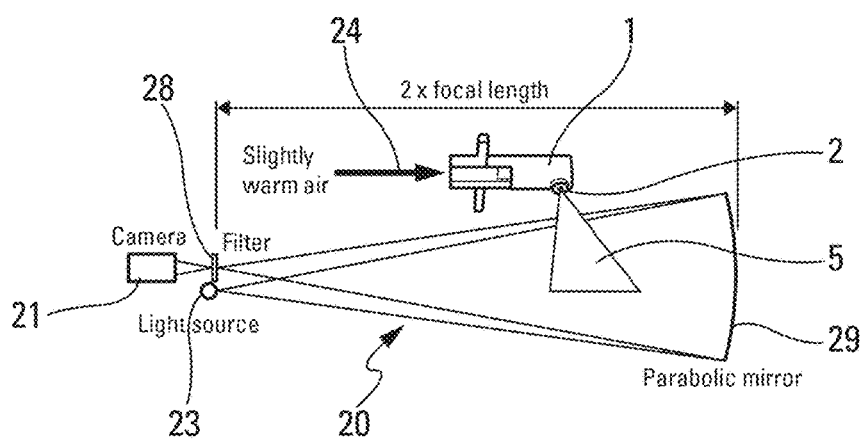
FIG. 3 is a diagrammatic view similar to the view in FIG. 2, of an advantageous variant embodiment.

FIGS. 2 and 3 show two variants of another advantageous embodiment in which the strioscopic setup includes a concave and/or parabolic mirror 29. This embodiment is more compact, with the light source 23 and the camera 21 arranged on one side, and the mirror 29 arranged on the opposite side. The overall operation is similar to the setup in FIG. 1.

It should be observed that the images obtained for displaying the spray may comprise static images (photographs) and/or videos.

In order to analyze the displayed sprays, the invention includes analyzer means 30 for determining whether or not the test-fluid spray coming from said spray head complies with predetermined specifications.

In particular, the analyzer means 30 may include measuring means for measuring the cone angle of the test-fluid spray.

Optionally, image-processing means for processing the displays of the test-fluid spray may be used to perform said analysis.

Said measuring and/or image-processing means can be part of specific softwares.

Thus, the predetermined specifications may include a predetermined spray cone angle, such that sprays having a cone angle that is greater than or equal to said predetermined spray cone angle are classed as being compliant, and sprays having a cone angle that is less than said predetermined spray cone angle are classed as being non-compliant.

Figure 4:
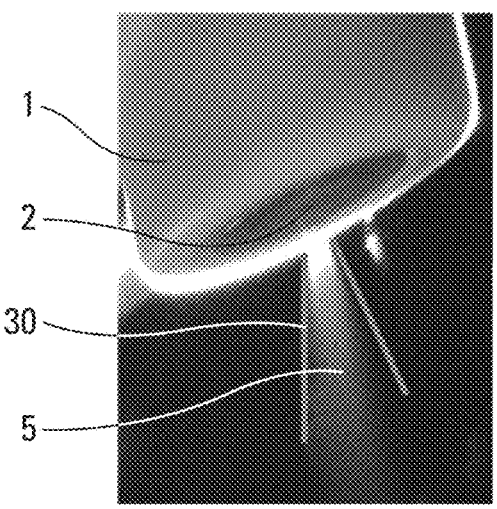
FIGS. 4 to 6 are diagrammatic views showing images obtained by a method of the invention.
Figure 5:
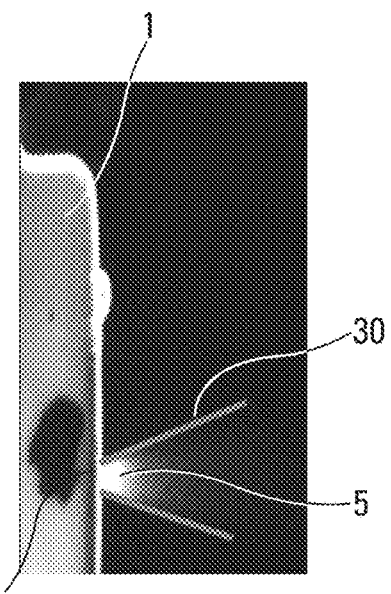
Figure 6:
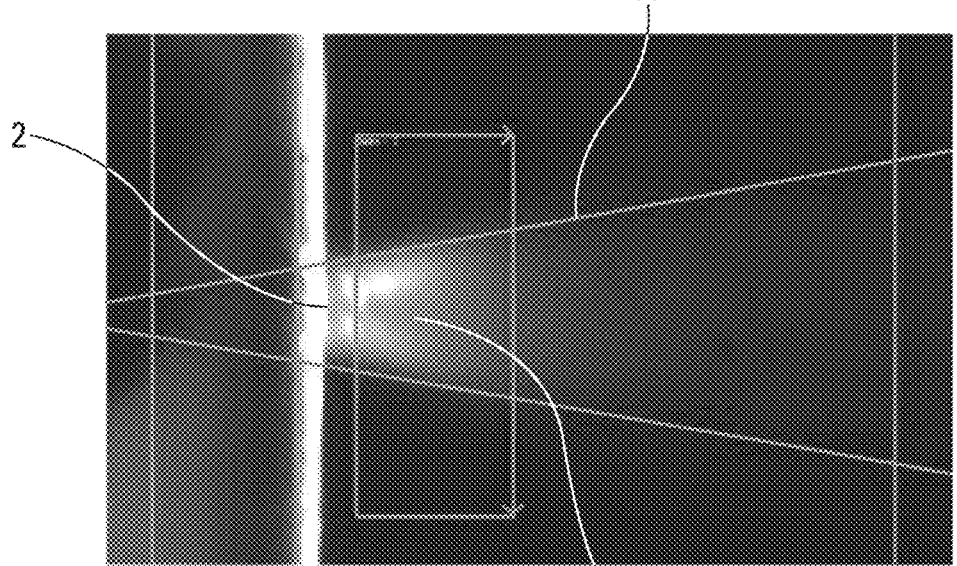

FIGS. 4 to 6 show images obtained with the method and the device of the invention, and in which it is possible to measure and/or to evaluate the cone angle of the spray, as shown by the cone lines.

Figure 7:
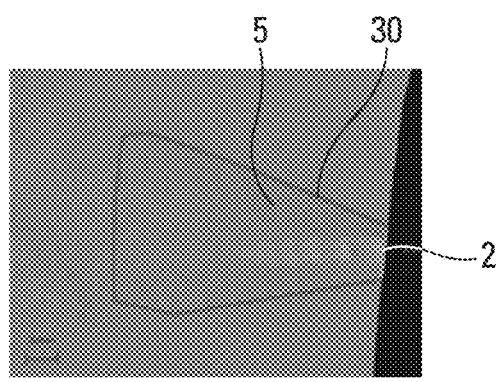
FIG. 7 is a diagrammatic view of a compliant test-fluid spray obtained by a method of the invention.
Figure 8:
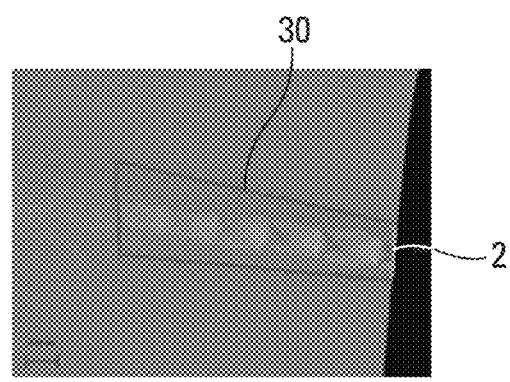
FIG. 8 is a view similar to the view in FIG. 7, showing a non-compliant test-fluid spray.

FIGS. 7 and 8 show images respectively showing a test-fluid spray that is classed as being compliant (FIG. 7) and a test-fluid spray that is classed as being non-compliant (FIG. 8).

Figure 9:
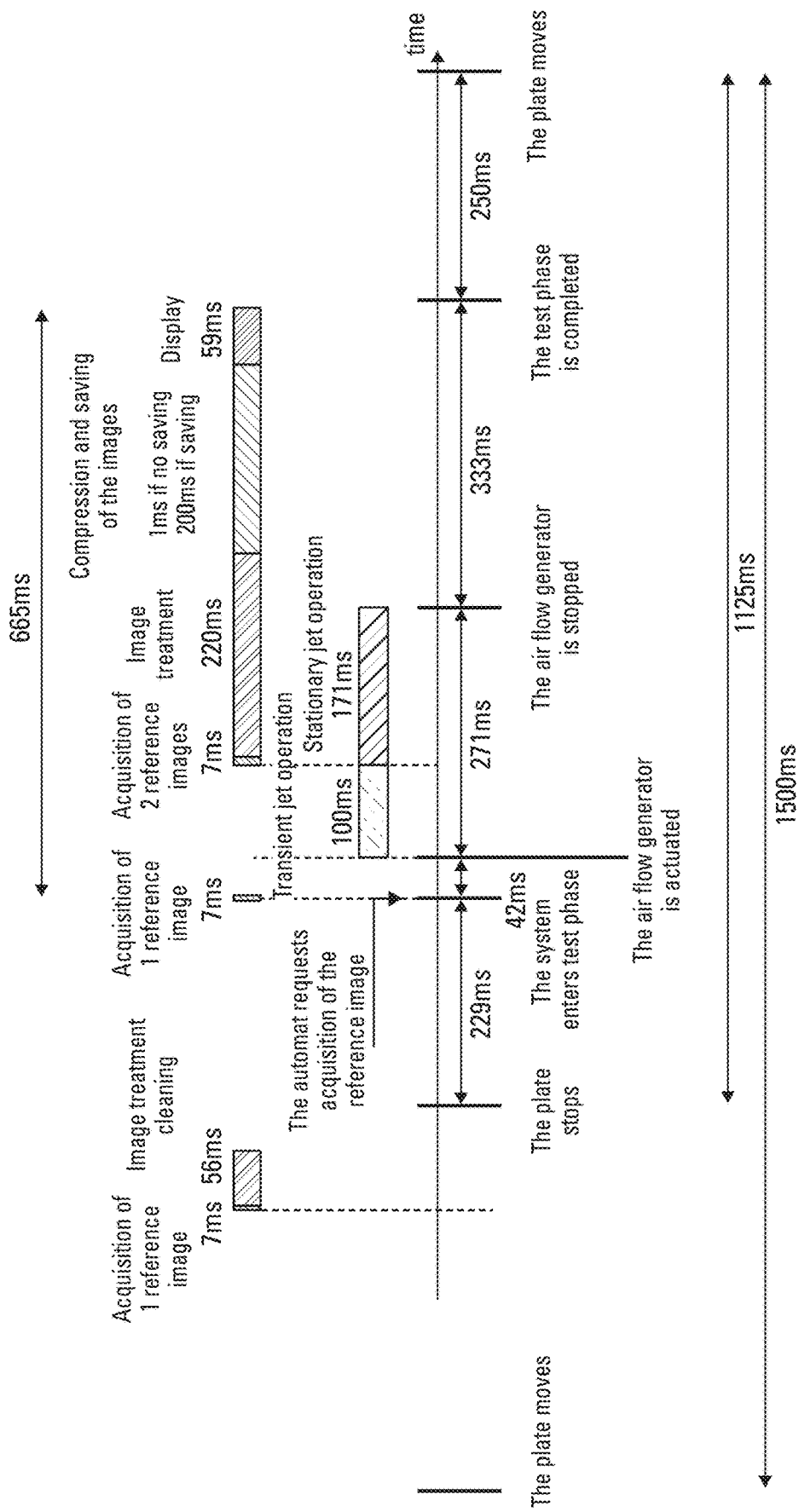
FIG. 9 shows a maximum cycle time for analyzing one spray head.

FIG. 9 shows a maximum cycle time for analyzing one spray head. This cycle time is in any case less than 1.5 seconds. If necessary, it can become even shorter, e.g. less than 1 second.

As can be seen on FIG. 9, a complete cycle includes several steps:
First, the plate supporting a spray head is moved to place a spray head in the analyzing device; typically, the time for this movement step is less than 500 milliseconds, advantageously about 375 milliseconds; if necessary, this time could be reduced to optimize the cycle time;
during this first step, the analyzing device can optionally take one reference image without any spray head, which allows to evaluate if some parts of the analyzing device must be cleaned;
once the plate supporting the spray head has stopped, the analyzing device makes a request for the acquisition of a reference image; typically, the time for this request step is less than 300 milliseconds, advantageously less than 250 milliseconds; if necessary, this time could be further reduced to optimize the cycle time;
the analyzing device takes one reference image before the air flow generator is actuated; typically, the time to take the reference image is less than 10 milliseconds, advantageously about 7 milliseconds;
after that first reference image without air flow has been taken, the air flow generator is actuated; typically, the time between the acquisition of a first reference image without air flow and the actuation of the air flow generator is less than 50 milliseconds, advantageously about 40 milliseconds;
once the air flow generator generates a stationary air flow, two reference images are taken; typically, the time between the actuation of the air flow generator and the generation of a stationary air jet is about 100 milliseconds; typically, the duration of the stationary air flow is less than 200 milliseconds, advantageously about 170 milliseconds; if necessary, this time could be further reduced to optimize the cycle time;
these two reference images are then superimposed with the first reference image taken without air flow, and an image processing step is started; typically, the time for the image processing is less than 250 milliseconds, advantageously about 220 milliseconds;
after the image processing, the images are compressed and eventually saved; the compression step is very short, about 1 millisecond, whereas the optional saving step typically takes about 200 milliseconds;
the compressed images are then displayed; typically, the time for the display step is less than 100 milliseconds, advantageously about 60 milliseconds;
thus, the total test phase, between the acquisition of the first reference image without air flow and the display of the compressed image, has a maximum duration less than 700 milliseconds with image saving and less than 500 milliseconds without image saving.

The present invention presents numerous advantages, and in particular:
it enables the spray from various types of spray device to be inspected automatically;
it enables said spray devices to be analyzed non-destructively;
it uses a setup that is compact and that can easily be adapted;
it uses components that are simple and standard, and thus generally inexpensive;
it has a very short cycle time, less than 1.5 seconds, advantageously less than 1 second;
it enables image processing to be robust, and that may be performed in real time; and
it guarantees good repeatability and good discrimination between compliant and non-compliant sprays.

The present invention is described above with reference to various advantageous embodiments, but naturally any useful modification could be applied thereto by the person skilled in the art, without going beyond the ambit of the present invention, as defined by the accompanying claims.

The invention claimed is:

1. A method of analyzing a spray generated by a spray device for spraying pharmaceutical fluid, the method comprising the following steps:
providing a spray head of a spray device for spraying pharmaceutical fluid, said spray head including a spray orifice;
causing a test fluid to pass through said spray head towards said spray orifice, said test fluid being air at a temperature that is different from ambient temperature;
displaying, by strioscopy, the flow of test fluid leaving said spray orifice; and
determining whether or not the test-fluid spray coming from said spray head complies with predetermined specifications based on information from said display of the test-fluid flow; and
wherein a complete cycle comprises following steps:
a plate supporting a spray head is moved to place a spray head in the analyzing device;

once the plate supporting the spray head has stopped, a request for the acquisition of a reference images is made;

one reference image is taken before the air flow generator is actuated;

after that first reference image without air flow has been taken, the air flow generator is actuated;

once the air flow generator generates a stationary air flow, two reference images are taken;

these two reference images are then superimposed with the first reference image taken without air flow, and an image processing step is started;

after the image processing, the images are compressed;

the compressed images are then displayed.

2. A method according to claim 1, wherein said analyzing step includes determining the cone angle of the test-fluid spray.

3. A method according to claim 1, wherein said analyzing step includes an image-processing step for processing said display of the test-fluid flow.

4. A method according to claim 1, wherein said predetermined specifications include a predetermined spray cone angle, such that test-fluid sprays having a cone angle that is greater than or equal to said predetermined spray cone angle are classed as being compliant, and test-fluid sprays having a cone angle that is less than said predetermined spray cone angle are classed as being non-compliant.

5. A method according to claim 1, wherein during said movement step, one reference image is taken without any spray head, which allows to evaluate if some parts of the analyzing device must be cleaned.

6. A method according to claim 1, wherein the time for said movement step is less than 500 milliseconds.

7. A method according to claim 1, wherein the time for said request step is less than 300 milliseconds.

8. A method according to claim 1, wherein the time to take a reference image is less than 10 milliseconds.

9. A method according to claim 1, wherein the time between the acquisition of a first reference image without air flow and the actuation of the air flow generator is less than 50 milliseconds.

10. A method according to claim 1, wherein the time between the actuation of the air flow generator and the generation of a stationary air jet is about 100 milliseconds.

11. A method according to claim 10, wherein the duration of said stationary air flow is less than 200 milliseconds.

12. A method according to claim 1, wherein the time for said image processing step is less than 250 milliseconds.

13. A method according to claim 1, wherein the time for the display step is less than 100 milliseconds.

14. A method according to claim 1, wherein said compressed images are saved.

15. A method according to claim 14, wherein said saving step takes about 200 milliseconds.

16. A method according to claim 14, wherein the total test phase, between the acquisition of the first reference image without air flow and the display of the compressed image, has a maximum duration which is less than 700 milliseconds with image saving and less than 500 milliseconds without image saving.

17. The method according to claim 1, wherein a cycle time for analyzing the spray generated by the spray device is less than 1.5 seconds.

18. The method according to claim 1, wherein a cycle time for analyzing the spray generated by the spray device is less than 1 second.

19. The method according to claim 1, wherein the time for said movement step is about 375 milliseconds.

20. The method according to claim 1, wherein the time for said request step is less than 250 milliseconds.

21. The method according to claim 1, wherein the time to take a reference image is about 7 milliseconds.

22. The method according to claim 1, wherein the time between the acquisition of a first reference image without air flow and the actuation of the air flow generator is about 40 milliseconds.

* * * * *